United States Patent
Amelse (10) Patent No.: US 9,902,666 B2
(45) Date of Patent: Feb. 27, 2018

(54) ENERGY EFFICIENT NAPHTHENE RECYCLE VIA THE USE OF A SIDE DRAW FRACTIONATION TOWER AND PARTIAL CONDENSATION

(71) Applicant: BP Corporation North America Inc., Houston, TX (US)

(72) Inventor: Jeffrey Amelse, Batavia, IL (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/105,693

(22) PCT Filed: Nov. 20, 2014

(86) PCT No.: PCT/US2014/066536
§ 371 (c)(1),
(2) Date: Jun. 17, 2016

(87) PCT Pub. No.: WO2015/094563
PCT Pub. Date: Jun. 25, 2015

(65) Prior Publication Data
US 2016/0311731 A1    Oct. 27, 2016

Related U.S. Application Data

(60) Provisional application No. 61/917,055, filed on Dec. 17, 2013.

(51) Int. Cl.
| | | |
|---|---|---|
| *C07C 5/27* | (2006.01) | |
| *C07C 7/12* | (2006.01) | |
| *B01D 3/00* | (2006.01) | |
| *B01D 5/00* | (2006.01) | |
| *B01J 19/24* | (2006.01) | |
| *C07C 7/04* | (2006.01) | |
| *C07C 7/09* | (2006.01) | |
| *C07C 7/00* | (2006.01) | |

(52) U.S. Cl.
CPC .............. *C07C 5/277* (2013.01); *B01D 3/009* (2013.01); *B01D 5/009* (2013.01); *B01D 5/0057* (2013.01); *B01J 19/24* (2013.01); *C07C 5/2702* (2013.01); *C07C 7/005* (2013.01); *C07C 7/04* (2013.01); *C07C 7/09* (2013.01); *C07C 7/12* (2013.01); *B01J 2219/00103* (2013.01); *B01J 2219/24* (2013.01)

(58) Field of Classification Search
CPC ........... C07C 15/08; C07C 5/277; C07C 7/12; C07C 7/04; C07C 7/09; B01D 3/009; B01D 5/0057; B01D 5/009; B01J 19/24; B01J 2219/00103; B01J 2219/24
See application file for complete search history.

(56) References Cited

U.S. PATENT DOCUMENTS

| | | | |
|---|---|---|---|
| 4,039,599 | A | 8/1977 | Gewartowski |
| 6,448,459 | B1 | 9/2002 | Magne-Drisch et al. |
| 6,878,855 | B2 | 4/2005 | Deckman et al. |
| 7,249,469 | B2 | 7/2007 | Porter |
| 2002/0107427 | A1* | 8/2002 | Doyle ................ C07C 7/005 585/828 |
| 2005/0171395 | A1 | 8/2005 | Huff, Jr. et al. |
| 2007/0299289 | A1 | 12/2007 | Bresler et al. |
| 2013/0144097 | A1 | 6/2013 | Bender et al. |

FOREIGN PATENT DOCUMENTS

| | | |
|---|---|---|
| CN | 1441759 | 9/2003 |
| FR | 2109342 | 5/1972 |
| WO | WO-02/04391 | 4/2002 |

* cited by examiner

*Primary Examiner* — Sharon Pregler
(74) *Attorney, Agent, or Firm* — Robert N. Carpenter (57) ABSTRACT

Processes for the energy efficient recycle of naphthenes in a paraxylene manufacturing process comprise partially condensing a reactor effluent and using a sidedraw tower apparatus. The naphthenes are efficiently separated into the sidedraw stream of the sidedraw tower apparatus. At least a portion of the sidedraw stream is directed to a paraxylene recovery section that produces a paraxylene product and a paraxylene lean stream comprising essentially all of the naphthenes in the sidedraw stream directed to the paraxylene recovery section. The paraxylene lean stream is recycled back to the reactor thereby preventing excessive loss of naphthenes from the processes.

18 Claims, 3 Drawing Sheets

FIG. 4

US 9,902,666 B2

ENERGY EFFICIENT NAPHTHENE RECYCLE VIA THE USE OF A SIDE DRAW FRACTIONATION TOWER AND PARTIAL CONDENSATION

CROSS-REFERENCE TO RELATED APPLICATION

This application claims priority to U.S. Provisional Application No. 61/917,055, filed Dec. 17, 2013, which is hereby incorporated by reference in its entirety,

FIELD

This disclosure relates to processes and apparatuses for the energy efficient recycle of naphthenes during the manufacture of paraxylene. Such processes and apparatuses include a partial condensation scheme and a sidedraw tower.

BACKGROUND

Paraxylene is a useful chemical intermediate that is oxidized to form terephthalic acid, which is a precursor to polyester. Paraxylene (pX) manufacturing units generally comprise three sections in a recycle loop: 1) a pX recovery section for recovering pX from streams comprising all three of the xylene isomers which produces a pX product stream and a pX lean stream; 2) an isomerization section comprising a xylene isomerization catalyst in a reactor that isomerizes the xylenes in the pX lean stream to near equilibrium; and 3) a fractionation section for separating byproducts produced in the reactor and/or present in the fresh feed. The fresh feed to pX units and thus to the pX recovery section generally also comprises ethylbenzene (EB) which is a structural isomer of the xylenes having a molecular formula that is the same as the xylene isomers. It is not practical to remove EB from these streams by distillation because its boiling point is very close to the xylene isomers. Thus, EB must be converted to xylenes or to byproducts that can be easily separated by distillation to prevent its build-up in the loop. There are several types of xylem isomerization catalysts that convert EB by differing routes. Ethylbenzene isomerization type catalysts provide a means for converting ethylbenzene to xylenes and offer high yields of paraxylene. Naphthenes, ring saturated compounds, are intermediates in the conversion of EB to xylenes and are at near equilibrium with the aromatics in the reactor effluent. These naphthene intermediates need to be efficiently recycled back to the reactor in order to prevent excessive xylene loss.

Prior configurations for paraxylene production and naphthene recycle are energy intensive and thus expensive to operate. For example, some prior art processes employ a separate naphthene tower. Thus, there is a need for an energy efficient process of recycling naphthenes in a paraxylene manufacturing process.

BRIEF SUMMARY

In one aspect, a process is provided comprising reacting in a reactor a reactor feed stream comprising xylene isomers, ethylbenzene, C8 naphthenes, and hydrogen over an ethylbenzene isomerization catalyst, such that a reactor effluent stream cot sing xylene isomers and C8 naphthenes is produced; cooling and separating the reactor effluent stream to form a first condensed liquid stream and a first vapor stream; and cooling and separating the first vapor stream to form a second condensed liquid stream and a second vapor stream. The process further comprises providing the first condensed liquid stream and the second condensed liquid stream to a sidedraw tower apparatus to produce a sidedraw stream comprising C8 aromatics and a portion of the C8 naphthenes; and recovering paraxylene from the sidedraw stream in a paraxylene recovery section.

In another spec a process for recycling naphthenes to a reactor is provided, the process comprising reacting in the reactor a reactor feed stream comprising xylene isomers, ethylbenzene, C8 naphthenes, and hydrogen over an ethylbenzene isomerization catalyst at reactor conditions wherein at least a portion of the ethylbenzene in the reactor feed stream is converted to xylem isomers, such that a reactor effluent stream comprising xylem isomers and C8 naphthenes is produced; cooling and separating the reactor effluent stream to form a first condensed liquid stream and a first vapor stream; and cooling and separating the first vapor stream to form a second condensed liquid stream and a second vapor stream. The process further comprises providing the first condensed liquid stream and the second condensed liquid stream to a sidedraw tower apparatus to produce a sidedraw stream comprising C8 aromatics and C8 naphthenes; recovering paraxylene from the sidedraw stream in a paraxylene recovery section; producing a paraxylene lean stream, wherein the paraxylene lean stream contains a portion of the C8 naphthenes; and recycling the paraxylene lean stream to the reactor.

In yet another aspect, an apparatus for recycling naphthenes to a reactor is provided, the apparatus comprising a preheater for preheating a liquid stream comprising ethylbenzene, xylene isomers, and C8 naphthenes to form a preheated liquid stream, wherein the preheated liquid stream is combined with a recycle gas stream comprising hydrogen to form a reactor feed stream; and a reactor for reacting the reactor feed stream to produce a reactor effluent stream comprising xylene isomers and C8 naphthenes. The apparatus further comprises a first cooling apparatus for cooling the reactor effluent stream to produce a cooled reactor effluent stream; a first separator drum for separating the cooled reactor effluent stream into a first condensed liquid stream and a first vapor stream; a second cooling apparatus for cooling the first vapor stream to produce a cooled first vapor stream comprising a vapor phase and liquid phase; and a second separator drum for separating the cooled first vapor stream into a second condensed liquid stream and a second vapor stream. The apparatus also comprises a sidedraw tower apparatus for receiving the first condensed liquid stream and the second condensed liquid stream and producing a sidedraw stream, wherein the sidedraw stream comprises C8 aromatics and greater than 70 percent of the C8 naphthenes; a paraxylene recovery section for separating the sidedraw stream into a paraxylene product stream and a paraxylene lean stream, wherein the paraxylene lean stream comprises substantially all of the C8 naphthenes in the sidedraw stream; and a recycling apparatus for recycling the paraxylene lean stream to the reactor.

DETAILED DESCRIPTION

Mixed xylenes is a term used for a stream comprising not only the xylene isomers, but also ethylbenzene (EB), which has the same molecular formula as the xylene isomers ($C_8H_{10}$), but is a structural isomer that has one ethyl group attached to a benzene, instead of two methyl groups in the case of the xylem; isomers. There are three isomers of xylenes: orthoxylene (oX), metaxylene (mX), and paraxylene (pX). Collectively, the xylene isomers and EB are called C8 Aromatics or C8A. Those skilled in the art will appreciate that the designator "CX" refers to a compound comprising X carbon atoms, "CX+" refers to compounds comprising X or greater carbon atoms, and "CX−" refers to compounds comprising X or fewer carbon atoms. C8A means aromatics having eight carbons. C9A+ means aromatics having nine or more carbons.

The order of normal boiling points for the C8A are from lowest to highest: EB pX, mX, and oX. However,all of the C8A boiling points are very close. Thus, it is not practical to separate the individual components of EB, pX, or mX in high purity from a mixture of C8A by distillation. oX does have a slightly higher boiling point than EB, pX, and mX, and thus can be economically separated from the other C8A by distillation, and is done so commercially. However. A recovery by distillation requires distillation towers with many trays and high reflux rates, and thus, high energy. Paraxylene is the isomer recovered in highest volume, because it is oxidized to terephthalic acid, which is a precursor to polyester, which is used to make fiber for clothing, plastic bottles for beverages, and films.

Paraxylene (pX) manufacturing units generally comprise three sections in a recycle loop: 1) a pX recovery section for recovering pX from streams comprising all three of the xylene isomers which produces a pX product stream and a pX lean stream; 2) an isomerization section comprising a xylene isomerization catalyst in a reactor that isomerizes the xylenes in the pX lean stream to near equilibrium; and 3) a fractionation section for separating byproducts produced in the reactor and/or present in the fresh feed. Paraxylene is usually recovered by crystallization or by selective adsorption, such as in the UOP Parex® technology.

Stand-alone pX units commonly derive their fresh feed as a C8 distillation cut from reformate formed from naphtha in a refinery catalytic reformer unit or from pyrolysis gasoline (pygas), which is a byproduct of olefin crackers. Pygas mixed xylenes generally have higher ethylbenzene content than mixed xylenes derived from reformate. The ethylbenzene content of pygas xylenes can be as high as 30-60 eight percent. The ethylbenzene content of mixed xylenes derived from reformate is generally about 12-20 weight percent.

pX units are often part of an aromatics manufacturing/production complex, which comprises a pX unit and other units that produce mixed xylenes feedstocks, such as: toluene (TOL) disproportionation (TDP) units; selective TDP (STDP) units that produce mixed xylenes having a very high percentage (>80 percent) of pX amongst the xylene: isomers (pX/XYL=% pX/(% pX+% mX+% oX), or TOL/A9+ or A9+ transalkylation units. Xylenes produced in TDP, STDP, TOL/A9+ or A9+ transalkylation units generally have a much lower ethylbenzene content than mixed xylenes derived from reformate, typically less than about 5 weight percent of ethylbenzene.

The feed to the pX recovery section is separated into pX product and a stream leaner in pX than the section feed known as raffinate in the case of selective adsorption or a reject filtrate stream in the case of crystallization (also called a paraxylene lean stream). This stream is recycled back to the reactor. A xylene isomerization catalyst is used in the reactor to isomerize the xylene isomers in the liquid feed to the reactor to near equilibrium and to convert at least a portion of ethylbenzene to xylenes or byproducts that can be readily separated from the C8 aromatics in the fractionation section to prevent ethylbenzene build-up fin the pX unit recycle loop. Ethylbenzene conversion is generally slower than xylene isomerization, and thus, xylene isomerization catalysts are often categorized by the manner in which they convert ethylbenzene. Several types of catalysts may be useful, including those that participate in ethylbenzene isomerization, ethylbenzene dealkylation, and ethylbenzene transalkylation.

The choice of xylene isomerization catalyst depends on feed availability as the three types of xylene isomerization catalysts mentioned above provide different yields of pX from a given amount of mixed xylenes feedstock, and also on the feed composition, in particular the ratio of ethylbenzene to xylene isomers in the feed. Currently, the most popular type of xylene isomerization catalyst is the ethylbenzene dealkylation type, which converts ethylbenzene via reaction with hydrogen to form benzene and ethane. Ethylbenzene isomerization catalysts are also useful, particularly when feed availability is scarce or when the feed contains high ethylbenzene content, such as stand-alone pX units processing C8A from reformate or pygas xylenes. This catalyst has the ability to convert ethylbenzene to xylene isomers. This type of catalyst combines a strong hydrogenation/dehydrogenation catalyst and an acid catalyst. The strong hydrogenation/dehydrogenation catalyst generally comprises a noble metal, most preferably platinum (Pt) or Pt alloyed or promoted by other elements. Popular alloying agents or promoters include but are not limited to tin and rhenium. Ethylbenzene is converted to xylenes by first saturating the aromatic ring of ethylbenzene over the hydrogenation/dehydrogenation catalyst to form ethylcyclohexane. The acid catalyst then isomerizes the ethylcyclohexane to dimethylcyclohexanes via alkylcyclopentane intermediates. The hydrogenation/dehydrogenation catalyst then dehydrogenates the dimethylcyclohexanes to form xylene isomers. Acid catalysts include but are not limited to chlorided alumina, silica-alumina, and molecular sieves. Mordenite is a popular type of molecular sieve used in ethylbenzene isomerization catalysts.

The strong hydrogenation/dehydrogenation catalyst generally establishes near equilibrium ring saturation between the ethylbenzene and xylenes and their corresponding ring saturated compounds, including ethylcyclohexane and the dimethylcyclohexanes, and the acid catalyst generally establishes a near equilibrium distribution of C8 naphthenes or C8N (comprising ethylcyclohexane, C8 alkylcyclopentanes, and the dimethylcyclohexanes). The C8 naphthenes are known collectively as a naphthene pool. The naphthene pool in the reactor effluent may be efficiently captured and recycled to the reactor to prevent net loss of valuable aromatics in the feed to low valued non-aromatic byproducts.

Side reactions such as transalkylation, cracking, and/or hydrocracking reactions typically produce some light aromatics (benzene and toluene), some light non-aromatics (C1-C6 paraffins and naphthenes (C1-C6 P&N), and heavy aromatics (C9A+). For example, xylene disproportionation produces toluene (TOL) and trimethylbenzene isomers (TMB, a C9A) from two xylene molecules. The light and heavy aromatic byproducts are removed in the pX unit fractionation section.

Ethylbenzene isomerization catalysts are available from a number of commercial suppliers. Some of the ethylbenzene isomerization catalysts that are or have been offered include the I-9, I-200, I-400 catalysts offered by UOP, and the Oparis™ and Zapheis™ family of catalysts offered by Zeolyst. The performance of these Zeolyst catalysts is known. See, e.g., Monique van der Zon, "Xylene Isomerization Catalyst and its Latest Developments", Zeolyst Users' Conference 2012. Sinopec has also developed its own ethylbenzene isomerization catalyst. RIC-200. See Q, Hou and Z. Liang, Petrochemical Technology (Chinese), 40, 1325 (2011) (hereinafter "Sinopec paper"), One common prior art configuration for a pX unit scheme employing an ethylbenzene isomerization catalyst includes the UOP Isomar® process isomerization section and the UOP Parex® pX recovery section. See R. A. Meyers, editor. Handbook of Petroleum Refining Processes, 3rd Edition, Mc-Graw-Hill (2004). In the UOP Isomar® process, the reactor effluent is cooled in a feed/effluent exchanger, and then further cooled to close to ambient temperature via air or water-cooling. The cooled reactor effluent is then typically directed to a single separator drum where recycle gas is separated from the condensed liquid. The recycle gas is compressed, combined with hydrogen make-up before or after compression, and then recycled to the reactor. The condensed liquid is directed to a fractionation section comprised of a deheptanizer tower and a xylene splitter tower. UOP considers the deheptanizer to be part of the isomer unit, and the xylene splitter to be part of the Parex® unit. However, it should be understood that the deheptanizer and xylene splitter towers are part of the fractionation section of a general pX unit. The deheptanizer and xylene splitter towers typically have separate reboilers. The deheptanizer separates a light liquid distillate stream comprising benzene (Bz), TOL, and light non-aromatics from the reactor effluent The C8N can be separated into the deheptanizer bottoms product, and then recycled o the reactor through the xylene column and Parex® unit. In this scheme, the C8N must be boiled overhead in the xylem splitter column, and again in the Parex® unit raffinate tower in order to end up in the raffinate stream for recycle to the reactor. However, the C8N generally have boiling points lower than the C8A, and thus, they can be taken overhead in the deheptanizer, and then recovered for recycle as the bottoms product of a separate naphthene tower. See A. Regular, "Commercial Application of OparisPlus in ZRCC," at the 2012 Zeolyst Users' Conference, Shanghai, China, May, 2012. A separate naphthene tower is needed in this case to separate the benzene and toluene and other light non-aromatic byproducts in the deheptanizer overhead liquid stream from the C8N.

Figure 1:
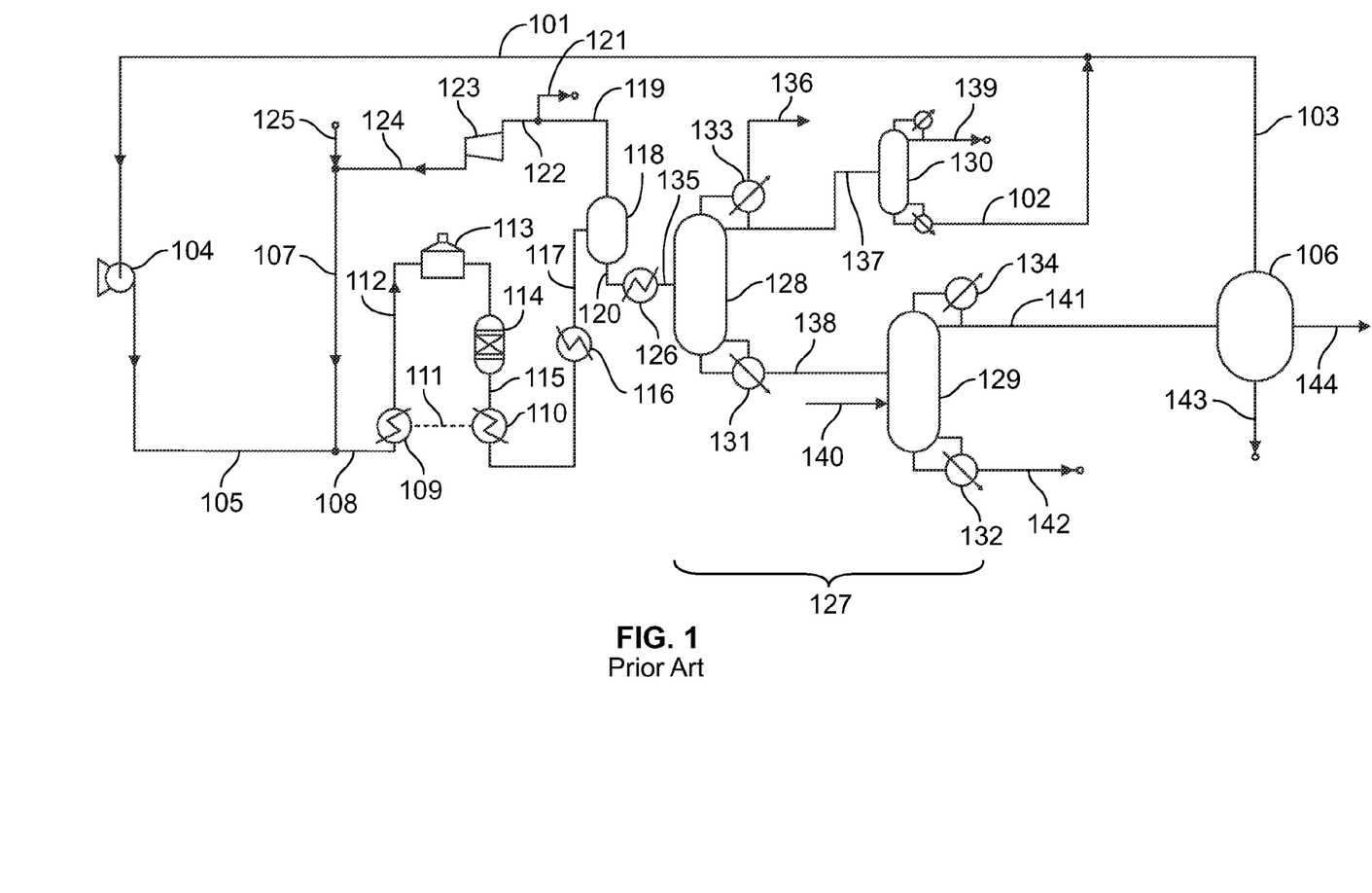
FIG. 1 is a prior art apparatus for producing paraxylene.

FIG. 1 illustrates the isomerization and fractionation sections of one prior art apparatus for producing paraxylene comprising a naphthenes tower, as discussed above. This scheme is energy intensive and requires capital for the naphthene tower.

The pressure of pX lean stream 101, which is the combination of a naphthene tower bottom product 102 and a pX lean stream 103, is increased via pump 104 to produce stream 105. Stream 103 is the pX lean stream exiting pX recovery section 106. Liquid stream 105 may be combined with a recycled gas stream 107 to produce a reactor feed stream 108. The reactor feed stream may be heated in a first heating unit 109, which may be the cold side of a heat exchanger. In this case, first heating unit 109 and first cooling unit 110 are the cold side and hot side of a heat exchanger commonly known as a feed/effluent heat exchanger, and dashed line 111 represents heat exchange between the two sides. In this case, the cold streams entering first heating unit 109 are heated by hot reactor effluent to produce a heated reactor feed stream 112. Streams 107 and 108 may be combined via separate nozzles feeding the cold side of a heat exchanger. The heated reactor feed stream 112 may be further heated in furnace 113 and may he fed to a reactor 114, where it may be reacted with hydrogen over a catalyst to produce a reactor effluent stream 115. The catalyst may be an ethylbenzene isomerization-type catalyst. The reactor effluent stream 115 may he provided to the first cooling unit 110 and a second cooling unit 116 to produce a cooled reactor effluent stream 117. The effluent from first cooling unit 110 is directed to second cooling unit 116 which may be an air or water cooling unit. The cooled reactor effluent stream 117 may be cooled to a close approach to ambient temperature, preferably to within about 5 degrees Celsius to about 30 degrees Celsius of ambient temperature. The cooled reactor effluent stream 117 may be directed to a separator drum 118 to produce a vapor stream 119 and a condensed liquid stream 120. A portion of the vapor stream 119 may be vented via stream 121, and the remainder (stream 122) may be compressed in compressor 123 to form compressed stream 124 and combined with make-up hydrogen stream 125 to form stream 107. The condensed liquid stream 120 may be preheated in unit 126, which may be a heat exchanger, and then may be provided to a fractionation section 127. The fractionation section 127 may comprise a deheptanizer 128, a xylene splitter 129, and a naphthene tower 130, wherein the deheptanizer 128 and the xylene splitter 129 have separate reboilers (a deheptanizer reboiler 131 and a xylene splitter reboiler 132). The depheptanizer 128 and the xylene splitter 129 have separate condensers (a deheptanizer condenser 133 and a xylene splitter condenser 134). If pX recovery section 106 is a selective adsorption unit, xylene splitter condenser 134 may comprise several condensers in series or parallel, and the condensing duty may be used to heat or reboil streams in the pX separation section or be used to produce steam.

The condensed liquid stream 120 maybe first preheated in unit 126 which may be one or more heater exchangers healed by hot process streams (not shown) or steam to produce preheated deheptanizer feed stream 135. Stream 135 may be provided to the deheptanizer 128, where it may be separated into a deheptanizer top products including a deheptanizer top vapor product (stream 136) and a deheptanizer lop liquid product (stream 137) and a deheptanizer bottom product 138. The deheptanizer bottom product (stream 138) may be substantially free of benzene and lighter boiling components, but may comprise a portion of the TOL in the reactor effluent, that may be removed in the pX recovery section 106. For example, if some TOL from the reactor effluent remains in stream 138, a portion may be removed in the pX recovery section 106 as stream 144. For example a portion of the TOL in stream 138 may be removed as the overhead product of a finishing tower in UOP Parex® pX separation section that produces pX product as the bottom stream of this tower. The deheptanizer top liquid product 137 may be provided to a naphthene tower 130 to produce a naphthene tower top product 139 and the naphthene tower bottom product 102. The naphthene tower top product 139 may comprise light non-aromatic byproducts and light aromatic byproducts such as benzene and toluene. The naphthene tower bottom product 102 may comprise C8 naphthenes. The C8 naphthenes may be recycled to the reactor 114.

Fresh feed comprising mixed xylenes feed may enter the pX unit as stream 140, which is directed to the xylene splitter 129. Fresh feed to a pX unit in an aromatics complex may also comprise C9A+. For example, fresh feed to the pX unit may comprise the C8A+ bottoms stream of an upstream reformate splitter. It may also comprise the C8A+ stream from a TDP, STDP, or TOL/A9+ TA unit. Reformate C8A+ and C8A+ form the other units may enter the tower on the same or separate feed trays. The deheptanizer bottom product 138 also be provided to the xylene splitter 129 where it may be separated into a xylene splitter top product 141 and a xylene splitter bottom product 142. The xylene splitter top product 141 may comprise primarily C8 aromatics and the xylene splitter bottom product 142 may comprise primarily C9 + aromatics. The xylene splitter bottom product 142 may be used as a byproduct stream useful as a high-octane gasoline blend stream. Alternatively, the xylene splitter bottom product 142 may be dealkylated and disproportioned by itself or with added toluene to make additional xylene isomer feed for the unit in a TOL/A9+ or A9+ transalkylation unit (not shown). The xylene splitter top product 141 may be provided to the paraxylene recovery section 106, which may produce a paraxylene product stream 143, the paraxylene lean stream 103, and a TOL concentrate stream 144. The pX lean stream 103 may be combined with the naphthene tower bottom product 102 and recycled to the reactor 114.

Alternately, the C8 naphthenes in deheptanizer feed stream 135 may be separated with high recovery into deheptanizer bottoms stream 138 and separated with high recovery into xylene splitter overhead stream 141, and sent to pX recovery section 106. In this case, the napththene tower 130, and streams 102 and 139 may be eliminated, and the naphthenes may be recycled to reactor 114 via stream 103.

pX recovery section 106 is shown as one block, but will generally comprise numerous equipment items. For a more detailed description of a Parex® selective adsorption pX recovery section, See R. A. Meyers, editor, Handbook of Petroleum Refining Processes, 3rd Edition, Mc-Craw-Hill (2004).

The acronym ERTVRE refers to the amount of energy required to vaporize the liquid condensed from the reactor effluent that is sent to the fractionation section. The fractionation section described in the above prior art scheme requires at least one times the ERTVRE to separate the light and heavy byproducts from the primarily C8A stream, and typically requires more than two times the ERTVRE.

An efficient xylene isomerization catalyst produces a minimal amount of C9A+ byproducts. Thus, the light byproducts, the C8A, and the C8N in the reactor effluent are typically more than 90 percent, and often more than 95 percent, and in many cases more than 99 percent of the hydrocarbons in the reactor effluent. In prior art fractionation sections, light byproducts and C8A are brought overhead in the deheptanizer and xylene splitter respectively. The C8N are brought overhead in the deheptanizer or the xylene splitter. If these towers were perfect separators, the minimum amount of energy required to bring these products overhead would be the amount of energy required to vaporize these products, and thus, would be close to one times the ERTVRE, since the C9A+ is less than 5 percent and in many cases less than about 1 percent of the condensable reactor effluent. Since these towers are not perfect separators, they require reflux, and the reflux ratios for these towers are typically greater than one and more typically greater than two. Thus in practice, the amount of energy required for the deheptanizer and xylene splitter towers is typically greater than times the ERTVRE for these prior art fractionation sections.

The present disclosure is directed to the use of a fractionation section comprising sidedraw tower or two separate towers operated essentially as a single sidedraw tower, which when combined with a scheme known as "Partial Condensation," can provide adequate separation of the byproducts from the reactor effluent of a reactor employing an ethylbenzene isomerization catalyst while requiring less than one times the ERTVRE, and typically less than about 60 percent of the ERTVRE. With this scheme, the C8N are efficiently captured in the primarily C8A stream which is sent to the pX recovery stream. The C8N are separated from the pX product in the pX recovery section into the pX recovery section pX lean stream, and are then recycled to the reactor, thus preventing their loss from the recycle loop.

Figure 2:
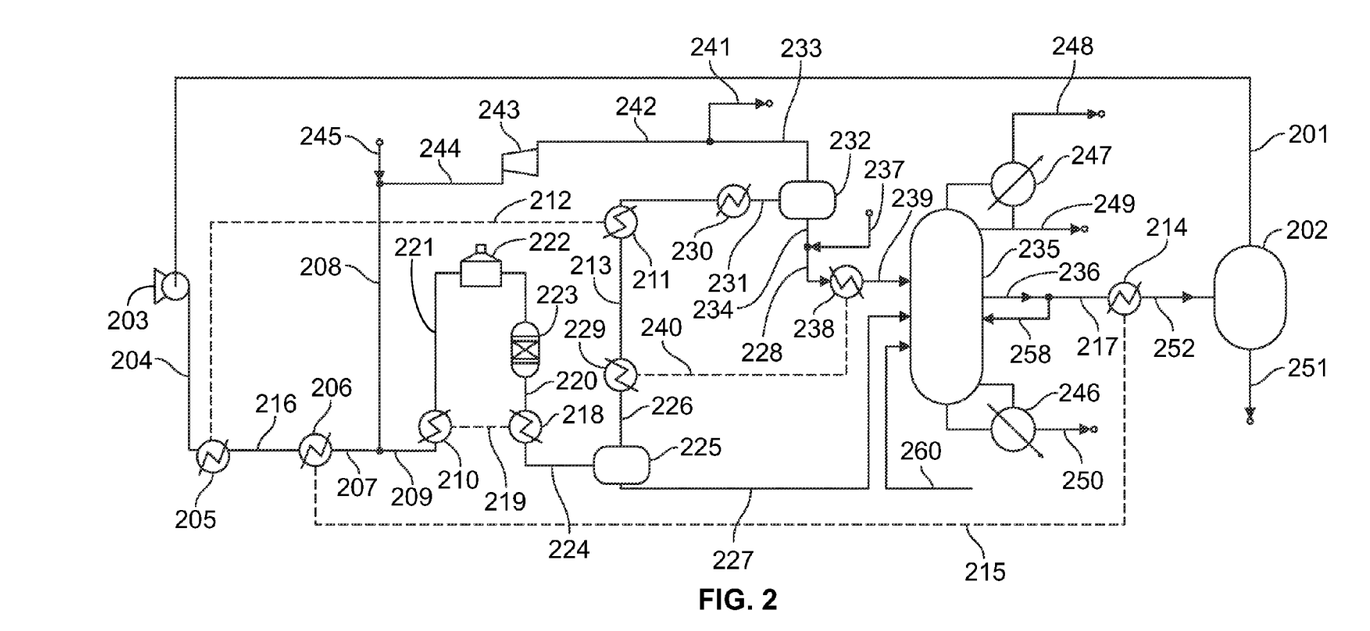
FIG. 2 is an apparatus for producing paraxylene with partial condensation and a single sidedraw tower.

FIG. 2 illustrates one configuration of an isomerization and fractionation section of the present disclosure, which comprises a single sidedraw tower and a crystallization pX recovery section. The pressure of pX lean (reject filtrate) stream 201 returning from the pX recovery section 202 is increased via pump 203 to produce liquid stream 204.

Figure 3:
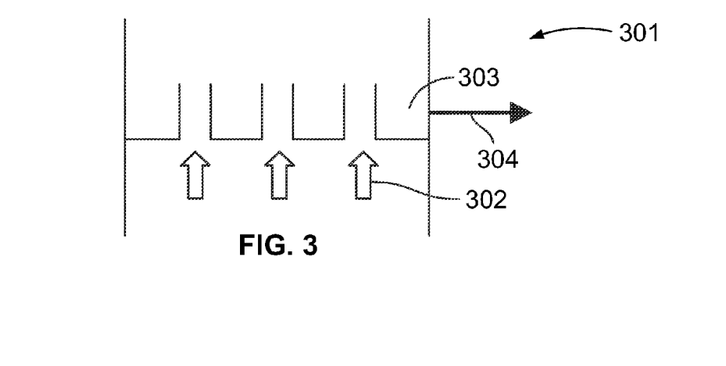
FIG. 3 is a sidedraw tray.

The sidedraw is typically withdrawn from a chimney A depiction of a chimney tray 301 is provided in FIG. 3. Vapor 302 from the tray below the chimney tray is allowed to pass through riser pipes and directed to the tray above the chimney tray. Liquid 303 from the tray above the chimney tray is directed to the space around the riser pipe. A controlled liquid sidedraw draw off 304 is taken to maintain a liquid level around the riser pipes.

In FIG. 2, the liquid stream 204 may be provided to a first heating unit 205 and a second heating unit 206 to produce a preheated liquid stream 207. The liquid stream 204 may comprise ethylbenzene, xylene isomers, and C8 naphthenes. The preheated liquid stream 207 may be combined with a recycled gas stream 208 to produce a reactor feed stream 209.

The reactor feed stream 209 may be further heated in a third heating unit 210. The first heating unit 205, the second heating unit 206, and the third heating unit 210 may be heat exchangers. Unit 205 may be the cold side of a heat exchanger having unit 211 as the corresponding hot side. In this case, dashed line 212 represents heat exchange between the hot side and the cold side, and thus, cold liquid stream 204 may be preheated by hot stream 213. Unit 206 may be the cold side of a heat exchanger having unit 214 as its corresponding hot side. In this case, dashed line 215 represents heat exchange between the hot side and the cold side, and thus cold liquid stream 216 may be preheated by hot sidedraw stream 217. Unit 210 may be the cold side of a heat exchanger having unit 218 as its corresponding hot side, and then dashed line 219 represents heat exchange between the hot side and the cold side, and thus, cold reactor feed stream 209 may be preheated by hot reactor effluent stream 220 to produce a preheated reactor feed stream 221. The temperature of stream 221 may be further increased by heating in unit 222, which may be a furnace, to the desired reactor inlet temperature.

The preheated reactor feed stream 221 may be fed to a reactor 223, where it may be reacted with hydrogen over a catalyst to produce reactor effluent stream 220. The catalyst may be an ethylbenzene isomerization-type catalyst. The ethylbenzene isomerization catalyst may comprise an acid catalyst and a strong hydrogenation catalyst capable of hydrogenating and dehydrogenating aromatic rings in the reactor feed s form a near equilibrium distribution of aromatics and naphthenes. The reactor effluent stream 220 may be provided to the first cooling unit 218 to produce a first cooled reactor effluent stream 224, which is at a temperature above that of cold reactor feed stream 209. The first cooling unit 218 may be a heat exchanger.

The first cooled reactor effluent stream 224 may be directed to a high temperature separator 225, where it may be separated to produce a first vapor stream 226 and a first condensed liquid stream 227. The first vapor stream 226 may be used to preheat the liquid stream 204 in the first heating unit 205, after first being used to preheat sidedraw tower feed stream 228. The first vapor stream 226 may be cooled in a second cooling until 229, a third cooling unit (heat exchanger unit 211), and a fourth cooling unit 230 to produce a cooled first vapor stream 231, which is cooled to a close approach to ambient temperature, preferably to within about 5 degrees Celsius to about 30 degrees Celsius of ambient temperature. Stream 231 may be a two-phase stream comprising both vapor and liquid. The second cooling unit 229 and the third cooling unit 211 may be heat exchangers. The fourth cooling unit 230 may be an air or water cooling unit. The cooled first vapor stream 231 may be directed to a low temperature separator 232, where it may be separated to produce a second vapor stream 233 and a second condensed liquid stream 234. The first condensed liquid stream 227 and the second condensed liquid stream 234 may be provided to a sidedraw tower apparatus 235. The first condensed liquid stream 227 may be provided to the sidedraw tower apparatus 235 at a location below a sidedraw stream 236 and the second condensed liquid stream 234 may be provided to the sidedraw tower apparatus 235 at a location above the sidedraw stream 236. The second condensed liquid stream 228 may be combined with fresh mixed xylenes feed to the pX unit, stream 237, acid preheated in unit 238 to produce a preheated second condensed liquid stream 239 before being fed to the sidedraw tower 235. Unit 238 miry be the cold side of a heat exchanger having unit 229 as the corresponding hot side. Dashed line 240 represents heat transfer between units 238 and 229.

If the fresh feed to the pX unit is contains less than about 3 weight percent A9+, then the fresh feed is preferably introduced via stream 237. Examples of mixed xylenes feed streams containing less than about 3 weight percent A9+ are mixed xylenes feed streams that conform to the specification of a maximum of 1 weight percent of C9 and higher boiling aromatic hydrocarbons of ASTM D5211-07 "Standard Specification for Xylenes for p-Xylene Feedstock." However, if a fresh feed stream to the pX unit comprises higher amounts of A9+, it is preferable to introduce that feed stream to the sidedraw tower apparatus at a tray location below the sidedraw via stream 260. pX unit fresh feed streams containing higher amounts of A9+ may include the A8+ bottoms stream of an upstream reformate splitter, or an A8+ stream from a TDP, STDP, TOL/A9+ or A9+ transalkylation unit. If there are multiple fresh feed streams to the pX unit, it may be desirable to direct them to the same or different feed trays in the sidedraw tower apparatus. Sending a feed stream to the sidedraw tower apparatus via stream 237 will save energy relative to feeding that stream via stream 260.

The second vapor stream 233 may comprise hydrogen and may be recycled to the reactor. A portion of stream 233 may be vented via stream 241. The balance (stream 242) may be compressed in compressor 243 to produce a compressor discharge stream 244. The compressor discharge stream 244 may be combined with hydrogen make-up stream 245 to form stream 208.

The sidedraw tower apparatus 235 may include a sidedraw tower reboiler 246 and a sidedraw tower condenser 247. The sidedraw to apparatus 235 may produce the sidedraw stream 236, a sidedraw tower off-gas stream 248, a top liquid product 249, and a sidedraw bottom product 250. The sidedraw stream 236 may comprise C8 aromatics and C8 naphthenes. The sidedraw stream 236 may also contain greater than 70 percent of the C8 naphthenes from the reactor effluent stream 220. The sidedraw tower top products may comprise an overhead vapor stream (sidedraw tower off-gas stream 248) comprising light ends and an overhead liquid stream (top liquid product 249) comprising C7-hydrocarbons. The sidedraw tower bottom product 250 may comprise C9+ hydrocarbons.

The sidedraw stream 236 (or at least a portion thereof) may be provided to the paraxylene recovery section 202, which may produce a paraxylene stream 251 and the paraxylene lean stream 201. pX recovery section 202 may be a crystallization pX recovery section. pX recovery section 202 is shown as a single block. However, it may comprise numerous equipment items, such as pumps, heat exchangers, crystallizers and/or re-slurry drums, solids separation devices, etc. The crystallizers may he jacketed crystallizers cooled by passage of a refrigerant through the jackets. The crystallization pX recovery section may include a refrigeration section, such as a cascaded ethylene/propane or ethylene/propylene refrigeration section. Some of the crystallizers may he cooled by ethylene refrigerant and some may be cooled by propane or propylene refrigerant.

The paraxylene lean stream 201 may contain a portion of the C8 naphthenes and may be recycled to the reactor 223. In an exemplary embodiment paraxylene lean stream 201 comprise at least 80 percent and preferably substantially all of the C8 naphthenes in the crystallization section feed stream 252. Stream 252 may he cooled in one or more cooling units (not shown) before being directed to pX recovery unit 202. A portion of the sidedraw stream 236 may also be used to preheat the liquid stream 204 in the second heating unit 206. That portion may be passed through unit 214, which may be the hot side of a heat exchanger having unit 206 as its corresponding cold side.

Figure 4:
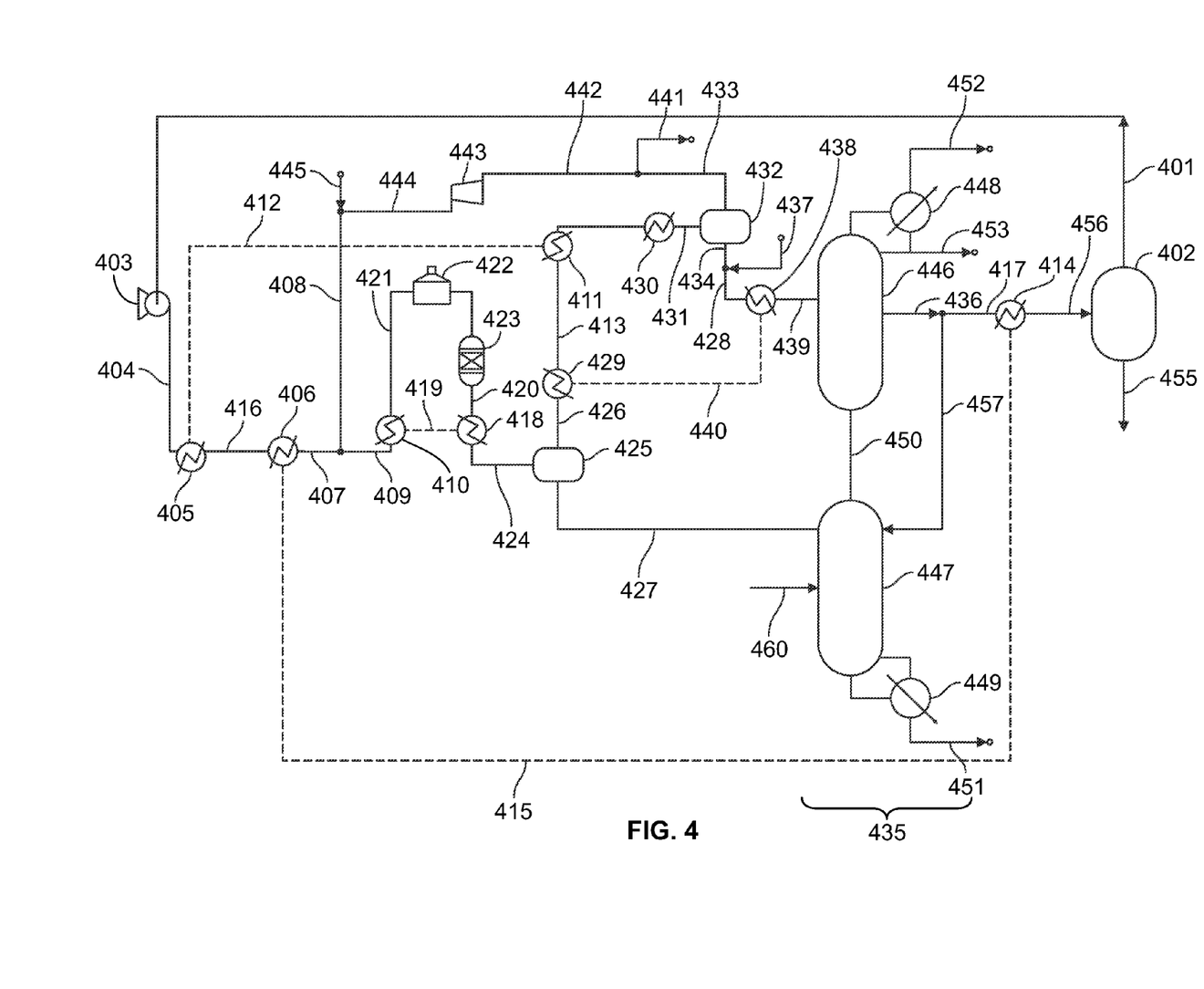
FIG. 4 is an apparatus for producing paraxylene with partial condensation and two towers operating essentially as a single sidedraw tower.

FIG. 4 illustrates a pX unit with a fractionation section 435 comprising two separate towers, a deheptanizer (unit 446) and a xylene splitter tower (unit 447), which operate essentially as a single sidedraw tower. The pressure of pX lean stream 401 returning from the pX separation section 402 is increased via pump 403 to produce stream 404. Liquid stream 404 may be provided to a first heating unit 405 and a second heating unit 406 to produce a preheated liquid stream 407. The liquid stream 404 may comprise ethylbenzene, xylene isomers, and C8 naphthenes. The preheated liquid stream 407 may be combined with a recycled gas stream 408 to produce a reactor feed stream 409.

The reactor feed stream 409 may be further heated in a third heating unit 410. The first heating unit 405, the second heating unit 406, and the third heating unit 410 may be heat exchangers. Unit 405 may be the cold side of a heat exchanger having unit 411 as the corresponding hot side. In this case, dashed line 412 represents heat exchange between the hot side and the cold side, and thus, cold liquid stream 404 may be preheated by hot stream 413. Unit 406 may be the cold side of a heat exchanger having unit 414 as its corresponding hot side. In this case, dashed line 415 represents heat exchange between the hot side and the cold side, and thus cold liquid stream 416 may be preheated by hot sidedraw stream 417. Unit 410 may be the cold side of a heat exchanger having unit 418 as its corresponding hot side, and then dashed line 419 represents heat exchange between the hot side and the cold side, and thus, cold reactor feed stream 409 may be preheated by hot reactor effluent stream 420 to produce a preheated reactor feed stream 421. The temperature of stream 421 may be further increased by heating in unit 422, which may be a furnace, to the desired reactor inlet temperature.

The preheated reactor feed stream 421 may be fed to a reactor 423, where it may be reacted with hydrogen over a catalyst to produce a reactor effluent stream 420. The catalyst may be an ethylbenzene isomerization-type catalyst. The ethylbenzene isomerization catalyst may comprise an acid catalyst and a strong hydrogenation catalyst capable of hydrogenating and dehydrogenating aromatic rings in the reactor feed stream form a near equilibrium levels of aromatics and corresponding naphthenes. The reactor effluent stream 420 may be provided to a first cooling unit 418 to produce a first cooled reactor effluent stream 424, which is at a temperature above that of stream 409. The first cooling unit 418 may lie a heat exchanger.

The first cooled reactor effluent stream 424 may be directed to a high temperature separator 425, where it may be separated to produce a first vapor stream 426 and a first condensed liquid stream 427. The first vapor stream 426 may he used to preheat the liquid stream 404 in first heating unit 405, after first being used to preheat sidedraw tower feed stream 428. The first vapor stream 426 may be cooled in a second cooling until 429, a third cooling unit (heat exchanger unit 411), and a fourth cooling unit 430 to produce a cooled first vapor stream 431, which is at a temperature that is at a close approach to ambient temperature, preferably within about 5 degrees Celsius to about 30 degrees Celsius of ambient temperature. Stream 231 may he a two phase stream comprising both vapor and liquid. The second cooling unit 429 and the third cooling unit 411 may be heat exchangers. The fourth cooling unit 430 may be an air or water cooling unit. The cooled first vapor stream 431 may be directed to a low temperature separator 432, where it may be separated to produce a second vapor stream 433 and a second condensed liquid stream 434. The first condensed liquid stream 427 and the second condensed liquid stream 434 may be provided to a sidedraw tower apparatus 435 to produce a sidedraw stream 436.

The second vapor stream 433 may comprise hydrogen and may be recycled to the reactor. A portion of stream 433 may be taken as a vent stream 441. The balance (stream 442) may be compressed in compressor 443 to produce compressor discharge stream 444. The compressor discharge stream 444 may be combined with hydrogen make-up stream 445 to form stream 408.

In this arrangement, the sidedraw tower apparatus 435 may include a deheptanizer unit 446, which also serves as a stabilizer, and a xylene splitter 447. The stabilizer 446 may include a stabilizer condenser 448 and the xylene splitter may include a xylene splitter reboiler 449. The deheptanizer/stabilizer reboiler and the xylene splitter condenser of the prior art scheme (FIG. 1) have been eliminated. The xylene splitter 447 may produce a xylene splitter top product 450 and a xylene splitter bottom product 451. The xylene splitter bottom product 451 may comprise C9A+ hydrocarbons. The xylene splitter top product 450 may be a vapor stream directed to the bottom of the stabilizer 446, essentially providing the reboil for the stabilizer 446. The bottom of the stabilizer 446 where the sidedraw liquid accumulates is basically equivalent to the area around the e chimney tray 301 (FIG. 3). Therefore, the stabilizer 446 and the xylene splitter 447 operate essentially as a single sidedraw tower. The stabilizer 446 may produce a stabilizer off-gas vapor top product comprising light ends 452 and stabilizer overhead liquid product 453 comprising C7— and a stabilizer bottom product, which is the sidedraw stream 436. The first condensed liquid stream 427 may be provided to the xylene splitter 447 and the second condensed liquid stream 434 may be provided to the stabilizer 446 at a location above the sidedraw stream 436. The second condensed liquid stream 434 may be combined with stream 437, which is fresh mixed xylenes feed to the pX unit, and preheated in unit 438 to produce a preheated second condensed liquid stream 439 before being directed to stabilizer 446. Unit 438 may be the cold side of a heat exchanger having unit 429 as the corresponding hot side. Dashed line 440 represents heat transfer between units 438 and 429.

If the fresh feed to the pX unit is contains less than about 3 weight percent A9+, then the fresh feed is preferably introduced via stream 437. Examples of mixed xylenes feed streams containing less than about 3 weight percent A9+ are mixed xylenes feed streams that conform to the specification of a maximum of 1 weight percent of C9 and higher boiling aromatic hydrocarbons of ASTM D5211-07 "Standard Specification for Xylenes for p-Xylene Feedstock." However, if a fresh feed stream to the pX unit comprises higher amounts of A9+, it is preferable to introduce that feed stream to tower 447 at a tray location below the sidedraw via stream 460. pX unit fresh feed streams containing higher amounts of A9+ may include the A8+ bottoms stream of an upstream reformate splitter, or an A8+ stream from a TDP, STDP, TOL/A9+ or A9+ transalkylation unit. If there are multiple fresh feed streams to the pX unit, it may be desirable to direct them to the same or different feed trays in the sidedraw tower apparatus. Sending a feed stream to the sidedraw tower apparatus via stream 437 will save energy relative to feeding that stream via stream 460.

The sidedraw stream 436 may comprise C8 aromatics and C8 naphthenes. The sidedraw stream 436 may also contain greater than 70 percent of the C8 naphthenes from the reactor effluent stream 420. The sidedraw stream 436 (or at least a portion thereof) may be provided to the paraxylene recovery section 402, which may produce a paraxylene product stream 455 and the paraxylene lean stream 401. The paraxylene lean stream 401 may contain a portion of the C8 naphthenes and may be recycled to the reactor 423. In an exemplary embodiment, the paraxylene lean stream 401 may comprise at least 80 percent and preferably substantially all of the C8 naphthenes in the crystallization section feed stream 456. Stream 456 may be further cooled in one or more cooling units (not shown) before being directed to pX recovery unit 402. A portion of the sidedraw stream 436 may also be used to preheat the liquid stream 404 in the second heating unit 406.

pX recovery section 402 is preferably a crystallization pX recovery section. It is shown as a single block. However, it will comprise numerous equipment items such as crystallizers, reslurry drums, pumps, heat exchangers, vessels, etc. The crystallizers may be jacketed crystallizers cooled by passage of a refrigerant through the jackets. The crystallization pX recovery section may include a refrigeration section, such as a cascaded ethylene/propane or ethylene/propylene refrigeration section. Some of the crystallizers may be cooled by ethylene refrigerant and some may be cooled by propane or propylene refrigerant.

In some embodiments, a portion of the first condensed liquid stream 227 or 427 may be provided to a location above the sidedraw stream 236 or 436, which will lead to a further reduction in reboiler duty, but will lead to poorer separation of lights and heavies from the sidedraw stream. It is preferable, although not necessary, to direct the portion of the first condensed liquid stream 227 or 427 to the same feed tray as the second condensed liquid stream 239 or 439. A portion of the second condensed liquid stream 239 or 439 may be provided to a location below the sidedraw stream 236 or 436. This will increase reboiler duty as any liquid sent to xylene splitter 447 below the sidedraw must be vaporized into the xylene tower overhead stream 450 of FIG. 4 or into the upper portion of the sidedraw tower 235 of FIG. 2. However, this will generally improve overall separation of byproducts from the sidedraw stream. A portion of the sidedraw stream 236 or 436 may be recycled to a location below the sidedraw stream. This increase separation of lights and heavies from the sidedraw, but will increase reboiler duty. The amount of stream 227 or 427 directed above the sidedraw-, the amount of stream 239 or 439 directed below the sidedraw, and the amount of a liquid stream 258 or 457 directed below the sidedraw may be optimized by an on-line optimizer.

The isomerization and fractionation sections of FIGS. 2 and 4 employ a "Partial Condensation" scheme. In a Partial Condensation scheme, condensable hydrocarbons in the reactor effluent are condensed in at least two separator drums. Condensable hydrocarbons mean the total hydrocarbons that are condensed from the reactor effluent in the separator drums. The reactor effluent is first cooled to a temperature substantially above ambient temperature such that a first condensed liquid stream is formed that represents only a portion of the condensable hydrocarbons and this first condensed liquid stream is separated in a first separator drum, the high temperature separator (HTS) drum, and the uncondensed vapor from this drum is then further cooled such that a second condensed liquid stream is formed and separated in a second drum, the low temperature separator (LTS) drum. In FIG. 2, unit 225 is the HTS drum and unit 232 is the LTS drum. In FIG. 4, unit 425 is the HTS drum and unit 432 is the LTS drum.

It may be desirable to condense less than about 70 percent, and preferably less than about 60 percent, for example less than about 50 percent, of the condensable hydrocarbons from the reactor effluent in the HTS drum. This can be achieved by using an inefficient feed/effluent exchanger (Units 210 and 218 or Units 410 and 418), or preferably by using a more efficient feed/effluent exchanger, but by preheating the recycle gas and/or heating the streams comprising the reactor feed to a higher temperature ahead of the feed/effluent exchanger. Using a more efficient feed/effluent exchanger is preferred because it leads to less energy consumption in the isomerization section. However, a less efficient feed/effluent heat exchanger is smaller, requires less surface area, and is thus less costly than a more efficient feed/effluent exchanger. Preheating these streams and using a less efficient feed/effluent exchanger leads to a hotter hot side effluent from the feed/effluent exchanger, and less condensation in the HTS drum.

In FIGS. 2 and 4, the isomerization liquid feed (streams 204 or 404) is first preheated by hot vapor coming off the HTS drum after it is used to preheat tower feed, and then by hot liquid side draw from the sidedraw tower apparatus. Preheating first with vapor from the HTS drum also serves to cool the HTS vapor stream ahead of final cooling by the final air or water cooler ahead of the LTS drum, which reduces the duty required by the final cooler and makes that exchanger smaller.

The xylene splitter tower of FIG. 4 receives liquid feed representing only a portion of the condensable hydrocarbons in the reactor effluent, and separates this stream into the xylene splitter tower overhead vapor stream, and the xylene splitter bottoms liquid stream (the A9+ byproduct stream). As noted above, an efficient ethylbenzene isomerization catalyst produces very little A9+ byproducts, so the bottoms stream is very small compared to the xylene tower feed stream.

In FIG. 4, the reboiler duty of the xylene splitter, i.e., the amount of energy required by the fractionation section is equal to the amount of energy that it takes to convert any liquid feed streams 427 and 457 to this tower to the vapor overhead stream 450 and the A9+ bottoms stream 451. When the fresh feed comprises mainly C8A with little C9A+, the amount of energy that it takes to generate the A9+ stream is very small, because this stream flow rate is small, and it only requires sensible heat to warm the components in the A9+ stream from the temperature of the HTS to the higher temperature of the A9+ stream. Since the heat of vaporization greatly exceeds sensible heat, most of the energy of the xylene tower reboiler is associated with converting the components in the liquid feed streams to the tower to the state of xylene splitter overhead vapor, i.e., the heat required to vaporize most of the HTS liquid stream to conditions of the vapor in stream 450. FIGS. 2 and 4 show that a portion of the sidedraw can be supplied as reflux to the section below the sidedraw. This stream may be directed to the tray below the sidedraw. However nay not be necessary to provide this reflux stream in order to provide the desired separation of light and heavy byproducts when the sidedraw serves as the primarily C8A feed stream to a crystallization pX recovery section.

If the sidedraw reflux stream is zero, and since the HTS liquid stream preferably represents less than about 50-70 percent of the condensable hydrocarbons in the reactor effluent, the amount of energy required to perform the separations in this scheme is less than about 50-70 percent of the ERTVRE. A lower reboiler duty compared to the prior art schemes means a lower boil-up rate, less traffic in both the upper and bottom sections of the sidedraw tower of FIG. 2 or both the stabilizer and xylene splitter lower of FIG. 4 and thus smaller diameter and less costly towers. In addition to energy savings, capital savings is another advantage of the fractionation scheme used in this disclosure.

In some embodiments, the hydrocarbons in the vapor stream of the HTS drum can be partially condensed in one or more additional middle temperature separator (MTS) drums before additional hydrocarbons are condensed in the LTS drum. For example, streams 213 or 413 may be two phase with vapor and liquid, and that stream may be passed to a MTS drum to separate vapor from liquid. The liquid separated in these MTS drums can be directed to feed trays either above or below the sidedraw. Directing them above the sidedraw leads to lower reboiler duty than directing them below the sidedraw, but reduces overall separation of byproducts from the sidedraw stream.

As noted above, a portion 253 of the sidedraw of FIG. 2 or a portion 457 of the bottoms of the stabilizer tower of FIG. 4 (the "sidedraw" of FIG. 4) can be directed below the sidedraw to provide reflux to the bottom portion of the sidedraw tower of FIG. 2 or the xylene splitter of FIG. 4. This will improve separation of the byproducts from the sidedraw stream but will lead to increased energy consumption since this reflux liquid must be vaporized. Reflux may also be provided internally in the sidedraw tower of FIG. 2 by, for example, over-spilling a chimney tray used to collect sidedraw liquid in the sidedraw tower. Preferably, no portion of the sidedraw is used as reflux in this manner.

In other embodiments, the fresh feed to the pX unit is a C8+ stream produced as the bottoms of a catalytic reforming unit reformate splitter, the fresh feed streams 237 of FIG. 2 or stream 437 of FIG. 4 may preferably be directed to a tray below the sidedraw in the bottom section of sidedraw tower 235 or xylem, splitter tower 447, as streams 260 or 460.

Using a separation scheme comprising a sidedraw tower as shown FIG. 2 or a two tower scheme that operates essentially as a single tower with a sidedraw as in FIG. 4 saves energy and capital cost relative to the sequential stabilizer, deheptanizer, and xylene splitter used in prior art separation schemes described above (e.g., FIG. 1). The inventor has surprisingly found that when using the fractionation schemes of FIG. 2 or 4 with partial condensation to separate byproducts from the effluent of a reactor employing an ethylbenzene isomerization catalyst, the C8 naphthenes can he recovered efficiently in the sidedraw while saving energy and capital relative to prior art sequential tower schemes. The naphthenes can then be passed through the pX recovery section and directed into the pX recovery pX lean stream and then efficiently recycled to the isomerization reactor, without the need for a separate naphthene tower.

EXAMPLES

Comparative Example 1

This example illustrates the amount of energy required to separate byproducts from the reactor effluent of an isomerization reactor containing an EB isomerization type catalyst using a sequential deheptanizer and xylene splitter as in the prior art.

The Aspen Plus process simulation program of Aspen Technology, Inc. is used to simulate part of an isomerization and a fraction sections of a pX unit using an EB isomerization type catalyst and sequential deheptanizer and xylene splitter towers as in the prior art that can produce a stream suitable as feed to a selective pX adsorption section. Selected stream conditions and compositions from the simulation are provided in Table 1 below.

The adsorption unit raffinate which is produced as an overhead stream of the raffinate tower in the pX selective adsorption section is cooled to 125 degrees Celsius to become the isomerization liquid feed. For purposes of the simulation, the C9A+ in the isomerization feed are assumed to comprise 0.05 weight percent methylethylbenzenes and 0.03 weight percent trimethylbenzenes.

The isomerization liquid feed is mixed with recycle gas that for the purposes of this simulation was assumed to be 100 mole percent hydrogen at an H2:Hc mole ratio of 4. The temperature of the combined recycle gas and isomerization liquid feed after being preheated by the sidedraw was 228 degrees Fahrenheit (108.9 degrees Celsius) The preheated isomerization liquid feed mixed with recycle gas is heated to a temperature of 640 degrees Fahrenheit (338 degrees Celsius) in a feed/effluent heat exchanger and further heated in a furnace to provide reactor inlet conditions of T=720 degrees Fahrenheit (382 degrees Celsius) and P=105 psig (825.3 kPa absolute (kPaa)).

The reactor is simulated by two ASPEN blocks, an ASPEN RSTOIC block and an ASPEN REQUIL block. Parameters are chosen for these blocks to provide a reactor effluent with a composition as shown in Table 1.

The REQUIL block parameters are set to provide a simulated equilibrium distribution of the xylene isomers and C8N isomers. Thus, the reactor blocks closely simulate the performance of the Sinopec RIC-200 catalyst as reported in the reference. See Q. Hou and Z. Liang, Petrochemical Technology (Chinese), 40, 1325 (2011).

The reactor effluent is cooled in a feed/effluent exchanger, and further cooled in an air cooler and sent to a vapor-liquid separator where it is separated at conditions of: T=43 degrees Celsius, P=728.7 kPa. The separator drum liquid is preheated to 204 degrees Celsius, and then sent to a deheptanizer.

The deheptanizer is simulated to contain 42 theoretical stages, and the feed is sent to theoretical stage 28 from the top. Design specifications for the deheptanizer are: 1) reflux Drum temperature=120 degrees Fahrenheit=48.9 degrees Celsius and 2) recovery of the C8N in the deheptanizer bottoms is 97.1 percent. Tower overhead pressure is simulated to be 55.5 psig=484.0 kPaa. Pressure drop to the reflux drum is assumed to be 3 psi=20.7 kPa. Tower pressure drop

TABLE 1

Comparative Example 1 Stream Compositions and Conditions Predicted by the Simulation

|  | Isom Liquid Feed | Reactor Inlet | Reactor Outlet | Separator Drum Liquid | Deheptanizer Overhead Liquid | Deheptanizer Bottoms Liquid | Xylene Splitter Overhead Liquid |
|---|---|---|---|---|---|---|---|
| Mass Flow, kg/hr |  |  |  |  |  |  |  |
| H2 | 0.0 | 34391.6 | 34022.3 | 26.0 | 0.1 | 0.0 | 0.0 |
| C1-C7 non-aromatics | 0.0 | 0.0 | 3871.8 | 1021.3 | 351.8 | 444.0 | 444.0 |
| BEN | 0.0 | 0.0 | 680.3 | 586.4 | 96.4 | 485.2 | 485.2 |
| TOL | 2358.7 | 2358.7 | 4399.8 | 4179.6 | 272.2 | 3902.8 | 3902.8 |
| EB | 48671.0 | 48671.0 | 37576.5 | 36863.8 | 302.0 | 36559.9 | 36559.9 |
| PX | 2903.0 | 2903.0 | 91156.2 | 89658.0 | 437.4 | 89218.0 | 89218.0 |
| MX | 260319.3 | 260319.3 | 200459.9 | 197343.3 | 802.9 | 196535.9 | 196535.9 |
| OX | 118570.3 | 118570.3 | 91613.0 | 90416.4 | 48.3 | 90367.9 | 90304.8 |
| C9A+ | 362.9 | 362.9 | 3297.6 | 3282.4 | 0.0 | 3282.4 | 183.6 |
| Total C8N | 20411.9 | 20411.9 | 20911.0 | 20036.6 | 573.7 | 19455.6 | 19455.6 |
| Total Flow, kg/hr | 453597.0 | 487988.8 | 487988.8 | 443413.8 | 2884.8 | 440251.7 | 437089.7 |
| Temperature, C. | 125.0 | 382.2 | 388.9 | 43.0 | 48.9 | 210.8 | 227.0 |
| Pressure, kPa | 901.1 | 825.3 | 790.8 | 728.7 | 463.3 | 511.6 | 687.4 | is assumed to be 4 psi=27.7 kPa. The deheptanizer bottoms temperature is calculated to be 210.8 degrees Celsius.

The deheptanizer bottoms liquid is passed through a clay treater to remove olefins, which is necessary to protect the molecular sieve used as adsorbent in the pX selective adsorption section. Following feed/effluent heat exchange around the clay treater, the deheptanizer bottoms temperature is adjusted to 191 degrees Celsius before being directed to a xylene splitter tower at theoretical stage 26 from the top. The xylene splitter is simulated to have 122 total theoretical stages. The xylene splitter overhead pressure is simulated to be 90 psig=721.9 kPaa. Pressure drop to the reflux drum is simulated to be 5 psi=34.5 kPa. Xylene splitter tower pressure drop is simulated to be 16 psi=110.3 kPa.

The xylene splitter overhead vapor temperature is calculated to be 230.5 degrees Celsius which is sufficient to reboil the deheptanizer tower and the extract, finishing, and raffinate towers of the selective adsorption section.

The design specifications for the xylene splitter tower simulation are 2 weight percent C8A in the xylene splitter tower bottoms, and 100 ppmw methylethylbenzene (MEB) in the C8A overhead stream. The C8A overhead stream is sent as feed to the pX selective adsorption section. The specification of 100 ppmw methylethylbenzenes is a typical specification for the pX selective adsorption feed to prevent contamination of the desorbent, which is typically p-diethylbenzene.

The calculated absorbed reboiler duty for the xylene splitter tower is 324.4 MMBTU/hr (342.2 GJ/hr). The calculated duty required to vaporize all of the separator drum liquid, which is equal to the total amount of condensables from the reactor effluent, from the conditions of the preheated feed to the deheptanizer to the conditions of the overhead vapor of the xylene splitter tower (P=90 psig (721.9 kPaa) is 144.60 MMBTU/hr (152.6 GJ/hr). Thus, the xylene splitter reboiler duty is equal to 2.24 times the ERTVRE. Essentially all of the C8 naphthenes in the deheptanizer bottoms are recovered in the C8A overhead stream of the xylene splitter. This stream is then sent to the pX selective adsorption section where essentially all of the C8 naphthenes are recovered in the raffinate and then are recycled to the reactor.

Example 1

The Aspen Plus process simulation program of Aspen Technology, Inc. was used to simulate part of an isomerization and a fraction sections of a crystallization pX unit using an EB isomerization type catalyst and employing partial condensation and a sidedraw fractionation tower consistent with the teaching of this invention. Details of the simulation are provided below.

The reactor liquid feed composition is shown in Table 2 below. An isomerization liquid feed rate of 1,000,000 lb/hr (453,592 kg/hr) is assumed for the simulation. This is the same flow rate and composition as for Comparative Example 1. Selected stream conditions and compositions from the simulation are provided in Table 2 below.

TABLE 2

| Example 1 Stream Compositions and Conditions Predicted by the Simulation | | | | | | | |
|---|---|---|---|---|---|---|---|
| | Isom Liquid Feed | Reactor Inlet | Reactor Outlet | HTS Liquid | LTS Liquid | Sidedraw Liquid | Stabilizer Overhead Liquid |
| Mass Flow, kg/hr | | | | | | | |
| H2 | 0.0 | 34391.6 | 34022.3 | 19.5 | 12.1 | 0.2 | 0.1 |
| C1-C7 non-aromatics | 0.0 | 0.0 | 3871.8 | 167.5 | 684.3 | 116.2 | 559.4 |
| BEN | 0.0 | 0.0 | 680.3 | 120.4 | 440.0 | 118.6 | 423.2 |
| TOL | 2358.7 | 2358.7 | 4399.8 | 1366.1 | 2790.7 | 2146.2 | 1981.8 |
| EB | 48671.0 | 48671.0 | 37576.5 | 17563.7 | 19409.5 | 36964.1 | 9.0 |
| PX | 2903.0 | 2903.0 | 91156.2 | 44273.6 | 45663.6 | 89927.4 | 9.3 |
| MX | 260319.3 | 260319.3 | 200459.9 | 98675.0 | 99286.0 | 197943.4 | 16.0 |
| OX | 118570.3 | 118570.3 | 91613.0 | 48185.2 | 42532.5 | 90703.5 | 1.3 |
| C9A+ | 362.9 | 362.9 | 3297.6 | 2296.6 | 993.6 | 1870.5 | 0.0 |
| Total C8N | 20411.9 | 20411.9 | 20911.0 | 7829.3 | 12187.0 | 19443.1 | 566.1 |
| Fraction CBN Recoverd in Sidedraw | | | | | | 0.971 | |
| Total Flow, kg/hr | 453597.0 | 487988.8 | 487938.8 | 220496.7 | 223998.9 | 439233.4 | 3566.4 |
| Temperature, degrees C. | 160.0 | 382.2 | 388.9 | 131.3 | 37.8 | 199.5 | 43.3 |
| Pressure, kPA | 901.1 | 825.3 | 790.8 | 749.4 | 687.4 | 515.0 | 342.6 |

The isomerization liquid feed is preheated in a partial condensation scheme similar to that of FIG. 2 to a final temperature of 320 degrees Fahrenheit (160 degrees Celsius), by heat exchange with vapor from the HTS drum and finally by heat exchange with hot sidedraw. The sidedraw temperature for this simulation s calculated to be 391.1 degrees Fahrenheit (199.5 degrees Celsius). For purposes of the simulation, the C9A+ in the isomerization feed are assumed to comprise 0.05 weight percent methylethylbenzenes and 0.03 weight percent trimethylbenzenes.

The isomerization liquid feed is mixed with recycle gas that for the purposes of this simulation is assumed to he 100 mole percent hydrogen at an H2:Hc mole ratio of 4. The temperature of the combined recycle gas and isomerization liquid feed after being preheated by the sidedraw is 228 degrees Fahrenheit (108.9 degrees Celsius) The preheated isomerization liquid feed mixed with recycle gas is heated to a temperature of 640 degrees Fahrenheit (338 degrees Celsius) in a feed/effluent heat exchanger and further heated in a furnace to provide reactor inlet conditions of T=720 degrees Fahrenheit (382 degrees Celsius) and P=105 psig (825.3 kPaa).

The reactor is simulated by two ASPEN blocks, an ASPEN RSTOIC block and an ASPEN REQUIL block. Parameters are chosen for these blocks to provide a reactor effluent with a composition as shown in Table 2. The REQUIL block parameters are set to provide a simulated equilibrium distribution of the xylene isomers and C8N isomers. Thus, the reactor blocks closely simulate the e performance of the Sinopec RIC-200 catalyst as reported in the reference. See Q. Hou and Z. Liang, Petrochemical Technology (Chinese), 40, 1325 (2011).

The reactor effluent is cooled in a feed/effluent exchanger, separated into a vapor and liquid stream in an HTS separator, and then the HTS drum vapor is further cooled via several heat exchangers and then separated into a vapor stream and a liquid stream in an LTS stream. Simulated conditions for the HTS separator are T=268.3 degrees Fahrenheit (131.3 degrees Celsius) and P-94 psig (749.4 kPaa). Simulated conditions for the LTS separator are T=100 degrees Fahrenheit (38 degrees Celsius) and P=85 psig (687.4 kPaa).

The simulated HTS liquid rate is 486109 lb/hr (220495 kg/hr) and the simulated LTS liquid rate is 493826 lb/hr (223996 kg/hr). Thus, the fraction of condensables in the HTS drum is 49.6 percent. The LTS liquid is preheated to 240 degrees Fahrenheit (116 degrees Celsius) before being directed to the sidedraw tower apparatus. For this case, 100,000 lb/hr (45359 kg/hr) of preheated LTS liquid is directed to the top tray of the xylene splitter (the tray below the sidedraw. This brings the total fraction of reactor effluent condensables fed to the xylene splitter than need to he vaporized to the conditions of the xylene splitter overhead vapor of 59.8 percent.

The stabilizer and xylene splitter are simulated to be configured to operate essentially as a single sidedraw tower as in FIG. 4. The stabilizer is simulated to have 51 theoretical stages, and the xylene splitter is simulated to have 31 theoretical stages. The feed tray of the stabilizer is simulated to be on the 16th theoretical stage from the top, and the feed tray of the xylem splitter is simulated to be its top tray, i.e., the tray below the sidedraw. Essentially no (0.001 lb/hr (0.0005 hr)) sidedraw reflux is prodded to the xylene splitter tower. The stabilizer overhead pressure is simulated to be 40 psig (377.1 kPaa). A tray pressure drop of 0.1 psi (0.69 kPa) is assumed for each theoretical stage of both towers. The calculated reboiler duty for the xylene splitter is 117.5 MMBTU/hr 124.0 GJ/hr). In a separate simulation, the preheated LTS liquid feed to the e stabilizer and the HTS liquid feed to the xylene splitter are combined and then vaporized in an Aspen Plus heater block at the xylene splitter overhead pressure and a vapor fraction of 1.0. The calculated duty required to vaporize the combined stream is 201.3 MMBTU/hr (212.4 GJ/hr). Thus, the reboiler duty is equal to only 0.584 times the ERTVRE.

The simulation predicts that 97.1 percent of the C8N in the HTS and LTS liquid streams are recovered in the sidedraw, and thus, would be efficiently recycled to the reactor via passage through the pX recovery section where essentially all of the C8N would end up in a crystallization pX recovery section pX lean stream, which becomes the isomerization liquid feed.

Comparative Example 2

For Comparative Example 1, as discussed above, the Aspen Plus simulation program is used to simulate part of an isomerization section and a fractionation section of a pX unit using an EB isomerization type catalyst and sequential deheptanizer and xylem splitter towers. The simulation does not attempt to close the recycle gas loop or the main liquid loop of the pX unit. The purpose of Comparative Example 1 is to show that naphthenes in the reactor effluent can be efficiently captured in the C8 stream which is the overhead of the xylene splitter tower, which may be sent to a selective adsorption unit for pX recovery. The reactor blocks in the simulation closely simulate the performance of the Sinopec RIC-200 catalyst as reported in the reference. See Q. Hou and Z. Liang, Petrochemical Technology (Chinese), 40, 1325 (2011) for a fixed feed having the composition provided in that paper. The reason for not closing the loops is that the paper did not provide the composition of the fresh feed to the pX unit.

The process simulated for Comparative Example 2 is as shown in FIG. 1 with two exceptions: 1) to specifications are chosen such that the C8 naphthenes are mainly recovered in stream 138 instead of stream 137, and thus, naphthene tower 130 and streams 102 and 139 are eliminated; and 2) as is typical for a UOP Parex® selective adsorption process, some toluene is dropped into the stabilizer bottoms stream 138. This TOL goes overhead in the xylene splitter tower 129 and is fed to the selective adsorption pX recovery section 106. Most of this TOL, is removed in a finishing tower in the Parex® unit as stream 144. Thus, the simulation includes a separator block that separates a portion of this TOL as a pure TOL stream from stream 103, such that the TOL in stream 101 is reduced to 0.52 weight percent, which matches the TOL in the liquid reactor feed in Column 1 of Table 8 of the Sinopec paper.

For Comparative Example 2, the recycle gas loop and main liquid loops are closed, fresh feed composition is estimated, and the reaction parameters in the ASPEN reactor blocks are varied to closely match both the liquid feed composition (Stream 105 of FIG. 1), and the reactor effluent composition as represented by the separator drum liquid composition (Stream 120 of FIG. 1). This matches the reactor feed and product composition of the first column of Table 8 of the Sinopec paper. By trial and error, it is possible to estimate the ratio of EB to xylene isomers in the fresh feed that will match the liquid feed EB content of the Sinopec paper. The ratio that is obtained is lower than typical for fresh feeds derived solely as a distillation cut from reformate, which indicates that the feed is likely a combination of reformate C8A+ and a C8A+ stream having low EB concentration, such as that from a TOL/A9+ transalkylation unit It is necessary to assume an amount of C9A+ in the fresh feed. An amount of C9A+ is assumed to give a typical ratio of C9A+ to C8A in combined feed streams for an aromatics complex from reformate xylenes and a C8A+ stream coming from a TOL/A9+ transalkylation unit. For the purposes of this example, the exact ratio of C9A+ to C8A in the fresh feed is not important, since the C9A+ will very efficiently be separated into the xylene splitter bottoms stream. However, it is important to use the same fresh feed composition when comparing Comparative Example 2 to Example 2.

Following the steps outlined above, it is found that a fresh feed having a composition in Table 3 along with iterated assumed reactor performance parameters can closely match both the reactor feed and product composition as reported in column 1 of Table 8 of the Sinopec paper, as shown in Table 4. The fresh feed rate for Comparative Example 2 is 389655 lb/hr (176746 kg/hr).

TABLE 3

Estimated Fresh Feed Composition

| Component | Weight Fraction |
|---|---|
| C9 P&N | 0.00644 |
| TOL | 0.00312 |
| EB | 0.05266 |
| pX | 0.11591 |
| mX | 0.26293 |
| oX | 0.14498 |
| Propylbenzenes | 0.00372 |
| Methylethylbenzenes | 0.08819 |
| Trimethylbenzenes | 0.21940 |
| Diethylbenzenes | 0.00364 |
| Dimethylethylbenzenes | 0.02356 |
| Tetramethylbenzenes | 0.02550 |
| C11A+ | 0.03801 |

TABLE 4

Comparing Simulated Feed and Product to That Reported in the Sinopec Paper

| | Sinopec Paper | | | | Simulation | | |
|---|---|---|---|---|---|---|---|
| | Feed Wt % | Effluent Wt % | Net Yield Wt % | | Feed Wt % | Effluent Wt % | Net Yield Wt % |
| NA | 4.49 | 5.42 | 0.93 | NA | 4.50 | 5.41 | 0.90 |
| B | 0.00 | 0.15 | 0.15 | B | 0.00 | 0.13 | 0.13 |
| TOL | 0.52 | 0.97 | 0.45 | TOL | 0.52 | 1.01 | 0.49 |
| EB | 10.73 | 8.27 | −2.46 | EB | 10.72 | 8.26 | −2.46 |
| pX | 0.64 | 19.64 | 19.00 | pX | 0.64 | 19.62 | 18.98 |
| mX | 57.39 | 44.53 | −12.86 | mX | 56.77 | 44.47 | −12.30 |
| oX | 26.14 | 20.30 | −5.84 | oX | 26.77 | 20.39 | −6.38 |
| C9A+ | 0.08 | 0.73 | 0.65 | C9A+ | 0.07 | 0.71 | 0.64 |
| Total | 99.99 | 100.01 | 0.02 | Total | 100.00 | 99.99 | −0.01 |
| % EBC | | | 22.93 | % EBC | | | 22.95 |
| XYL | 84.17 | 84.47 | 0.30 | XYL | 84.18 | 84.48 | 0.30 |
| EB/C8A | 11.31 | 8.92 | | EB/C8A | 11.29 | 8.91 | |
| pX/XYL | 0.76 | 23.25 | | pX/XYL | 0.76 | 23.22 | |
| % C8A Loss | | | 2.28 | % C8A Loss | | | 2.28 |
| % Ring Loss | | | 0.93 | % Ring Loss | | | 0.90 |
| EB/XYL | 0.1275 | 0.0979 | | EB/XYL | 0.1273 | 0.0978 | |

Other relevant specifications for Comparative Example 2 are as follows: The separator drum liquid is preheated to a temperature of 204 degrees Celsius before being fed to theoretical stage 28 from the top of the deheptanizer, which had a total of 42 theoretical stages. The calculated absorbed duty for the deheptanizer is 76.7 MMBTU/hr (80.9 GJ/hr). The following specifications are assumed for the deheptanizer tower simulation: 1) an overhead condenser outlet temperature of 120 degrees Fahrenheit (48.9 degrees Celsius); 2) 1 weight percent C8A in the deheptanizer overhead liquid product stream; and 0.55 weight percent TOL in the deheptanizer bottoms stream. A selective adsorption pX unit will typically drop some TOL into the deheptanizer bottoms stream, and this TOL will largely end up in the extract s of the selective adsorption it, and later most will be removed as a TOL product from the selective adsorption finishing TOL as stream 144 of FIG. 1. The TOL is taken as an overhead stream of this tower and the pX product is taken as the bottoms stream.

The design specifications for the xylene splitter tower are 2 weight percent C8A in the C9A+ xylene splitter bottoms stream and 100 ppmw of MEB in the C8A overhead of the xylene splitter tower, which is the feed to the selective adsorption unit.

The deheptanizer bottoms (stream 138 of FIG. 1) are fed to theoretical stage 26 from the top of the xylene splitter tower, which has 112 theoretical stages. The combined fresh feed is assumed to be at a temperature of 178.3 degrees Celsius, having come as the bottoms of upstream towers and is fed to theoretical stage 66 from the top (stream 140 of FIG. 1).

The absorbed duty for the deheptanizer tower is calculated to be 76.6 MMBTU/hr (80.9 GJ/hr) and the absorbed duty for the xylene splitter tower is calculated to be 343.3 MMBTU/hr (362.2 GJ/hr). The calculated duty required to vaporize the separator drum liquid at the pressure of the overhead vapor from the top tray of the xylene splitter (P=90 psig (721.9 kPaa)) is 121.8 MMBTU/hr (128.5 GJ/hr). Thus, the reboiler duty for the xylene splitter is 2.82 limes the ERTVRE. The combined absorbed duty for the deheptanizer and the xylene splitter is 3.45 times the ERTVRE.

Some calculated stream compositions, flow rates, and conditions for Comparative Example 2 are provided in Table 5.

TABLE 5

Comparative Example 2 Stream Compositions and Conditions Predicted by the Simulation

| | Isom Liquid Feed | Reactor Inlet | Reactor Outlet | Separator Drum Liquid | Deheptanizer Overhead Lliquid | Deheptanizer Bottoms Lliquid | Xylene Splitter Overhead Liquid |
|---|---|---|---|---|---|---|---|
| Mass Flow, kg/hr | | | | | | | |
| H2 | 0.0 | 28557.4 | 28279.4 | 21.8 | 0.1 | 0.0 | 0.0 |
| C1-C7 non-aromatics | 0.0 | 22102.2 | 25665.1 | 3561.2 | 1962.3 | 0.0 | 0.0 |
| C9 non-aromatics | 11003.3 | 11301.5 | 10171.4 | 9873.1 | 4.0 | 9869.1 | 11007.3 |
| BEN | 11.2 | 89.9 | 564.2 | 485.5 | 443.1 | 11.2 | 11.2 |
| TOL | 1965.3 | 2168.9 | 4014.0 | 3810.5 | 1725.3 | 2042.5 | 2593.2 |
| EB | 40510.9 | 41123.6 | 31848.8 | 31236.3 | 17.6 | 31218.5 | 40525.8 |
| PX | 2422.9 | 3680.7 | 75468.4 | 74210.3 | 12.6 | 74197.6 | 94678.4 |
| MX | 214555.5 | 217248.9 | 170898.6 | 168202.8 | 20.8 | 168182.0 | 214634.9 |
| OX | 101191.1 | 102227.2 | 78157.9 | 77121.0 | 0.7 | 77120.6 | 101228.8 |
| C9A+ | 265.8 | 277.8 | 2711.6 | 2699.6 | 0.0 | 2699.6 | 265.9 |
| Total C8N | 6021.0 | 6356.1 | 7355.4 | 7020.2 | 979.9 | 6023.2 | 6023.2 |
| Fraction C8N Recovered in Xylene | | | | | | | 0.858 |

TABLE 5-continued

Comparative Example 2 Stream Compositions and Conditions Predicted by the Simulation

|  | Isom Liquid Feed | Reactor Inlet | Reactor Outlet | Separator Drum Liquid | Deheptanizer Overhead Lliquid | Deheptanizer Bottoms Lliquid | Xylene Splitter Overhead Liquid |
|---|---|---|---|---|---|---|---|
| Splitter Overhead Liquid |  |  |  |  |  |  |  |
| Total Flow, kg/hr | 377947.5 | 435134.3 | 435134.3 | 378242.8 | 5166.4 | 371364.0 | 470969.8 |
| Temperatrue, degrees C. | 121.5 | 383.0 | 390.0 | 43.0 | 48.9 | 211.6 | 227.9 |
| Pressure kPaa | 1034.2 | 825.3 | 790.8 | 728.7 | 463.3 | 511.6 | 687.4 |

The simulation predicts that 85.8 percent of the naphthenes in the separator drum liquid that is fed to the fractionation towers are recovered in the xylene splitter overhead liquid.

Example 2

For Example 1, as discussed above, the Aspen Plus simulation program is used to simulate part of an isomerization section and a fraction section of a pX unit using an EB isomerization type catalyst, a sidedraw tower, and a partial condensation scheme. The simulation does not attempt to close the recycle gas loop or the main liquid loop of the pX unit. The purpose of Example 1 is to show that naphthenes in the reactor effluent can be efficiently captured in the sidedraw stream, which may be sent to a crystallization pX recovery unit. The reactor blocks in the simulation closely match the performance of the Sinopec RIC-200 catalyst as reported in the reference. See Q. Hou and Z. Liang, Petrochemical Technology (Chinese), 40, 1325 (2011) for a fixed feed having the composition provided in that paper.

In this example, the performance of an EB isomerization catalyst in a pX unit with a crystallization pX recovery section is estimated to show that the C8 naphthenes in the reactor effluent can be efficiently captured in the sidedraw of a pX unit using a sidedraw tower and partial condensation. The recycle gas and main liquid recycle loops are converged. The same fresh feed composition and flow rate as estimated in Comparative Example 2 and provided in Table 3 is used. The simulation simulates the process shown in FIG. 4 with the following exception: the fresh feed composition is the same as that estimated in Comparative Example 2, and is fed to theoretical stage 22 of Column 447 as stream 460 of FIG. 4, which has a total of 41 theoretical stages. No feed is fed via line 437.

Other relevant specifications for Example 2 are as follows: 100,000 lb/hr (45,359 kg/hr) sidedraw is provided as reflux stream 457 to the top tray of Tower 447. The isomerization liquid fed is preheated to 115.6 degrees Celsius in block 405, then to 182.2 degrees Celsius in block 406 as part of a partial condensation scheme. The combined liquid feed and recycle gas (Stream 409) is heated by hot reactor effluent to 641.4 degrees Celsius in block 409. Furnace 422 heats the reactor feed to 383 degrees Celsius.

As noted above, for a crystallization unit, the weight percent pX in the crystallization section reject filtrate, which becomes the liquid stream fed to the reactor, is higher than in a selective adsorption unit due to the eutectic limitation. For Comparative Example 2, the weight percent pX in the selective adsorption nit raffinate stream, which becomes the liquid feed to the reactor, is 0.64 weight percent to be consistent with Column 1 of Table 8 of the Sinopec paper. For Example 2, the concentration of pX in e reject filtrate stream 401 is assumed to be 9 weight percent.

For Example 2, the performance of the EB isomerization catalyst in a crystallization pX unit is estimated by reducing the fraction of EB converted to xylenes until the ratio of EB/XYL in the reactor feed, where XYL is the sum of the weight percent of the xylene isomers in the liquid reactor feed, is slightly greater than the ratio of EB/XYL for Comparative Example 2 to insure sufficient driving force for converting EB to xylenes. As an approximation, the conversions of all side reactions are assumed to be reduced by the same fraction from their values determined for Comparative Example 2. An Aspen REQUIL block is used to establish equilibrium between the C8A and the C8N and amongst the C8N isomers.

The estimated reactor feed and effluent composition for this example is compared to that in Column 1 of Table 8 of the Sinopec paper in Table 5.

TABLE 6

Comparing Simulated Feed and Product to That Reported in the Sinopec Paper

| | Sinopec Paper | | | | Simulation | | |
|---|---|---|---|---|---|---|---|
| | Feed Wt % | Effluent Wt % | Net Yield Wt % | | Feed Wt % | Effluent Wt % | Net Yield Wt % |
| NA | 4.49 | 5.42 | 0.93 | NA | 5.27 | 5.84 | 0.58 |
| B | 0.00 | 0.15 | 0.15 | B | 0.02 | 0.10 | 0.09 |
| TOL | 0.52 | 0.97 | 0.45 | TOL | 0.41 | 0.66 | 0.25 |
| EB | 10.73 | 8.27 | −2.46 | EB | 10.92 | 9.60 | −1.31 |
| pX | 0.64 | 19.64 | 19.00 | pX | 9.00 | 19.19 | 10.19 |
| mX | 57.39 | 44.53 | −12.86 | mX | 50.03 | 43.47 | −6.56 |

TABLE 6-continued

Comparing Simulated Feed and Product to That Reported in the Sinopec Paper

| | Sinopec Paper | | | | Simulation | | |
|---|---|---|---|---|---|---|---|
| | Feed Wt % | Effluent Wt % | Net Yield Wt % | | Feed Wt % | Effluent Wt % | Net Yield Wt % |
| oX | 26.14 | 20.30 | −5.84 | oX | 23.48 | 19.94 | −3.54 |
| C9A+ | 0.08 | 0.73 | 0.65 | C9A+ | 0.87 | 1.18 | 0.31 |
| Total | 99.99 | 100.01 | 0.02 | Total | 105.26 | 105.83 | 0.00 |
| % EBC | | | 22.93 | % EBC | | | 12.03 |
| XYL | 84.17 | 84.47 | 0.30 | XYL | 82.51 | 82.59 | 0.09 |
| EB/C8A | 11.31 | 8.92 | | EB/C8A | 11.68 | 10.41 | |
| pX/XYL | 0.76 | 23.25 | | pX/XYL | 10.91 | 23.23 | |
| % C8A Loss | | | 2.28 | % C8A Loss | | | 1.31 |
| % Ring Loss | | | 0.93 | % Ring Loss | | | 0.58 |
| EB/XYL | 0.12748 | 0.097905 | | EB/XYL | 0.13230 | 0.11625 | |

Note that for the crystallization case (Example 2), EB conversion is reduced to about 12 percent to achieve a ratio of EB/XYL in the reactor feed that is greater than that for the selective adsorption case (Comparative Example 2, where the EB conversion is 22.9 percent). This will increase recycle rates. However, at the lower EB conversion, it is estimated that the percent C8A loss, the percent ring loss, and the extent of other side reactions are reduced, which may lead to an improvement in pX yield.

Exact catalyst performance in the crystallization unit will depend on catalyst choice and optimized reactor conditions, including the percent EB conversion. The purpose of this example is to show that by using a sidedraw tower and partial condensation in a crystallization pX unit, the C8 naphthenes can be efficiently recovered in the sidedraw and thus efficiently recycled to the reactor with greatly reduced reboiler energy than required for the selective adsorption Comparative Example 2.

Some stream compositions and conditions for Example 2 are included in Table 7.

The calculated absorbed reboiler duty for tower 447 is 201.0 MMBTU/hr (212.1 GJ/hr). The calculated duty required to convert the HTS and LTS separator drum liquids into vapor at the conditions of the overhead of Tower 447 (60 psia=413.7 kPaa) is 375.0 MMBTU/hr (395.6 GJ/hr). Thus, the ERTVRE is 0.536. Note that while recycle rates are higher for the crystallization case (compare isomerization liquid feed rates for Comparative Example 2 and Example 2), the absolute duty required to perform the separations in the fractionation section is much less for crystallization Example 2 than it is for the selective adsorption Comparative Example 2.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the

TABLE 7

Example 2 Stream Compositions and Conditions Predicted by the Simulation

| | Isom Liquid Feed | Reactor Inlet | Reactor Outlet | HTS Liquid | LTS Liquid | Sidedraw Liquid | Stabilizer Overhead Liquid |
|---|---|---|---|---|---|---|---|
| Mass Flow, kg/hr | | | | | | | |
| H2 | 0.2 | 53615.6 | 53309.9 | 28.6 | 23.1 | 0.2 | 0.1 |
| C1-C7 non-aromatics | 74.3 | 29736.3 | 33297.8 | 510.0 | 3111.4 | 74.4 | 1397.9 |
| C9 non-aromatics | 20097.7 | 20559.4 | 19436.7 | 7697.4 | 11277.3 | 20102.0 | 0.5 |
| BEN | 77.2 | 213.6 | 855.0 | 123.3 | 595.2 | 77.2 | 567.9 |
| TOL | 3430.8 | 3711.4 | 5501.3 | 1415.4 | 3805.0 | 3431.5 | 2236.6 |
| EB | 77227.2 | 78295.4 | 69035.7 | 27482.6 | 40484.0 | 77243.5 | 22.4 |
| PX | 63949.9 | 65732.1 | 137991.0 | 57318.3 | 78890.0 | 156642.0 | 13.3 |
| MX | 354899.8 | 358667.8 | 312406.3 | 131664.2 | 176972.2 | 354976.4 | 21.2 |
| OX | 166475.6 | 167836.3 | 142850.9 | 64902.0 | 76587.1 | 166511.4 | 0.8 |
| C9A+ | 6975.9 | 6997.5 | 9100.7 | 5681.0 | 3398.1 | 6977.4 | 0.0 |
| Total C8N | 17344.0 | 18359.3 | 19939.5 | 5944.8 | 12978.9 | 17347.8 | 1518.2 |
| Fraction C8N Recovered in Sidedraw | | | | | | 0.917 | |
| Total Flow, kg/hr | 710550.7 | 803724.0 | 803724.0 | 302767.4 | 408122.6 | 803383.8 | 5779.0 |
| Temperatrue, degrees C. | 38.0 | 383.0 | 387.1 | 137.3 | 37.8 | 200.0 | 48.9 |
| Pressure kPaa | 1170.0 | 873.5 | 839.1 | 797.7 | 721.9 | 515.0 | 342.6 |

The simulation predicts that 91.7 percent of the naphthenes in the separator drum liquids that are fed to the sidedraw tower are recovered in the sidedraw stream.

known or customary practice in the art to which this invention pertains and which fall within the limits of the following claims.

What is claimed is:

1. A process for recycling naphthenes to a reactor, the process comprising:
   reacting in the reactor a reactor feed stream comprising xylene isomers, ethylbenzene, C8 naphthenes, and hydrogen over an ethylbenzene isomerization catalyst at reactor conditions wherein at least a portion of the ethylbenzene in the reactor feed stream is converted to xylene isomers, such that a reactor effluent stream comprising xylene isomers and C8 naphthenes is produced;
   cooling and separating the reactor effluent stream to form a first condensed liquid stream and a first vapor stream;
   cooling and separating the first vapor stream to form a second condensed liquid stream and a second vapor stream;
   providing the first condensed liquid stream and the second condensed liquid stream to a sidedraw tower apparatus to produce a sidedraw stream comprising C8 aromatics and C8 naphthenes;
   recovering paraxylene from the sidedraw stream in a paraxylene recovery section; producing a paraxylene lean stream, wherein the paraxylene lean stream contains a portion of the C8 naphthenes; and
   recycling the paraxylene lean stream to the reactor.

2. The process of claim 1, wherein the first condensed liquid stream is provided to the sidedraw tower apparatus at a location below the sidedraw stream, and wherein the second condensed liquid stream is provided to the sidedraw tower apparatus at a location above the sidedraw stream.

3. The process of claim 1, wherein a portion of the first condensed liquid stream is provided to a location above the sidedraw stream.

4. The process of claim 1, wherein a portion of the second condensed liquid stream is provided to a location below the sidedraw stream.

5. The process of claim 1, wherein a portion of the sidedraw stream is recycled to a location below the sidedraw stream.

6. The process of claim 1, wherein the ethylbenzene isomerization catalyst comprises an acid catalyst and a strong hydrogenation catalyst capable of hydrogenating and dehydrogenating aromatic rings in the reactor feed stream to form a near equilibrium distribution of aromatics and naphthenes.

7. The process of claim 1, further comprising
   preheating a liquid stream comprising ethylbenzene, xylene isomers, and C8 naphthenes to form a preheated liquid stream;
   combining the preheated liquid stream with a recycle gas stream comprising hydrogen to form the reactor feed stream; and
   providing the reactor feed stream to the reactor.

8. The process of claim 7, wherein the liquid stream is preheated with the sidedraw stream.

9. The process of claim 8, wherein the liquid stream is preheated with the first vapor stream.

10. The process of claim 1, further comprising recycling the second vapor stream to the reactor.

11. The process of claim 1, wherein the mass of the first condensed liquid stream is less than about 70 percent of the sum the masses of the first condensed liquid stream and the second condensed liquid stream.

12. The process of claim 1, further comprising separating greater than 70 percent of the C8 naphthenes in the reactor effluent stream into the paraxylene lean stream.

13. The process of claim 1, wherein the sidedraw tower apparatus comprises a single distillation tower.

14. The process of claim 1, wherein the sidedraw tower apparatus comprises more than one distillation tower.

15. The process of claim 1, further comprising:
   producing in the sidedraw tower apparatus an overhead vapor stream comprising light ends, an overhead liquid stream comprising C7-hydrocarbons, a bottoms stream comprising C9+ hydrocarbons, and the sidedraw stream comprising C8 aromatics and containing greater than 70 percent of the C8 naphthenes from the reactor effluent stream.

16. An apparatus for recycling naphthenes to a reactor, the apparatus comprising:
   a preheater for preheating a liquid stream comprising ethylbenzene, xylene isomers, and C8 naphthenes to form a preheated liquid stream, wherein the preheated liquid stream is combined with a recycle gas stream comprising hydrogen to form a reactor feed stream;
   a reactor for reacting the reactor feed stream to produce a reactor effluent stream comprising xylene isomers and C8 naphthenes;
   a first cooling apparatus for cooling the reactor effluent stream to produce a cooled reactor effluent stream;
   a first separator drum for separating the cooled reactor effluent stream into a first condensed liquid stream and a first vapor stream;
   a second cooling apparatus for cooling the first vapor stream to produce a cooled first vapor stream comprising a vapor phase and liquid phase;
   a second separator drum for separating the cooled first vapor stream into a second condensed liquid stream and a second vapor stream;
   a sidedraw tower apparatus for receiving the first condensed liquid stream and the second condensed liquid stream and producing a sidedraw stream, wherein the sidedraw stream comprises C8 aromatics and greater than 70 percent of the C8 naphthenes;
   a paraxylene recovery section for separating the sidedraw stream into a paraxylene product stream and a paraxylene lean stream, wherein the paraxylene lean stream comprises C8 naphthenes from the sidedraw stream; and
   a recycling apparatus for recycling the paraxylene lean stream to the reactor.

17. The apparatus of claim 16, wherein the sidedraw tower apparatus comprises a single distillation tower.

18. The apparatus of claim 16,
   wherein the sidedraw tower apparatus comprises a bottom tower and a top tower, and
   wherein an overhead vapor stream from the bottom tower is provided to the bottom of the top tower and the sidedraw stream is produced as a bottoms liquid stream of the top tower.

* * * * *